US008628702B2

(12) United States Patent
Hagenbuch et al.

(10) Patent No.: US 8,628,702 B2
(45) Date of Patent: Jan. 14, 2014

(54) SUPPORTING PASTE

(75) Inventors: Konrad Hagenbuch, Salez (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 1191 days.

(21) Appl. No.: 11/643,004

(22) Filed: Dec. 20, 2006

(65) Prior Publication Data

US 2007/0193475 A1 Aug. 23, 2007

(30) Foreign Application Priority Data

Dec. 23, 2005 (DE) .......................... 10 2005 062 192

(51) Int. Cl.
- *A61C 13/08* (2006.01)
- *A61C 8/00* (2006.01)
- *B28B 1/00* (2006.01)
- *B28B 3/00* (2006.01)
- *B28B 5/00* (2006.01)
- *C04B 33/32* (2006.01)
- *C04B 33/36* (2006.01)
- *C04B 35/64* (2006.01)

(52) U.S. Cl.
USPC ........ 264/19; 264/681; 433/201.1; 433/202.1

(58) Field of Classification Search
USPC .............. 432/258; 264/16–20, 435, 436, 603, 264/681, 345, 346; 106/35; 433/201.1, 433/202.1
See application file for complete search history.

(56) References Cited

U.S. PATENT DOCUMENTS

| | | | | |
|---|---|---|---|---|
| 1,965,299 A | * | 7/1934 | Patterson | 51/304 |
| 2,000,285 A | * | 5/1935 | Hoffmann | 106/35 |
| 2,670,573 A | * | 3/1954 | Sullivan, Jr. | 65/116 |
| 3,122,483 A | * | 2/1964 | Rosenthal | 424/49 |
| 3,518,206 A | * | 6/1970 | Stiles et al. | 502/64 |
| 4,219,617 A | * | 8/1980 | Wallshein | 433/8 |
| 4,647,600 A | | 3/1987 | Kawahara et al. | |
| 4,652,312 A | * | 3/1987 | Grossman et al. | 106/35 |
| 4,693,748 A | * | 9/1987 | Kobayashi et al. | 106/35 |
| 4,772,436 A | * | 9/1988 | Tyszblat | 264/19 |
| 5,154,613 A | * | 10/1992 | Cohen | 433/228.1 |
| 5,236,496 A | | 8/1993 | Shinuya et al. | |
| 6,087,281 A | | 7/2000 | Merkel | |
| 6,106,747 A | | 8/2000 | Wohlwend | |
| 6,371,762 B1 | | 4/2002 | Foser | |
| 6,391,813 B1 | | 5/2002 | Merkel | |
| 6,740,267 B1 | * | 5/2004 | Sekino et al. | 264/19 |
| 7,374,422 B2 | | 5/2008 | Hopfauf et al. | |
| 2003/0059742 A1 | | 3/2003 | Webster et al. | |
| 2004/0148916 A1 | | 8/2004 | Merkel | |
| 2006/0150598 A1 | * | 7/2006 | Ichikawa et al. | 55/523 |
| 2007/0269762 A1 | * | 11/2007 | Kim et al. | 433/9 |

FOREIGN PATENT DOCUMENTS

DE 1467061 A1 4/1969

* cited by examiner

*Primary Examiner* — Carol M Koslow
*Assistant Examiner* — Matthew E Hoban
(74) *Attorney, Agent, or Firm* — Ann M. Knab; Thad McMurray

(57) ABSTRACT

A supporting paste containing a component (A) which loses water in a temperature range between 110° C. and 1100° C., a component (B) which is geometrically stable at temperatures between 110° C. and 1100° C., solvent and auxiliary agents. Also, the preparation of such a supporting paste and to its use in particular in the field of dental technology.

10 Claims, No Drawings

SUPPORTING PASTE

BACKGROUND OF THE INVENTION

1. Field of the Invention

The present invention relates to compositions for supporting pastes, their preparation and use in the field of dental technology.

2. Description of the Related Art

Sintering or crystallization of glassy or glass ceramic molded parts is carried out at high temperatures, sometimes close to the softening or even melting point of these materials. In order to avoid warpage of the molded parts, it is necessary to support these parts.

It is known from the prior art to use so-called heat protection pastes in high temperature processes. With these pastes, however, the main function consists primarily in guaranteeing protection of the molded part to be treated thermally or its structural environment. These products, however, are intended for industrial use and are thus not suitable for use in the manufacture of dental products. Customary constituents of such pastes are glass fibers, glass powders, ceramic powders, and water and a thickening agent, such as, for example, various celluloses.

The disadvantage of these pastes consists especially in the fact that some ingredients of the pastes "adhere" to the molded parts and are intercalated into the surface of the molded part such that these residues of the pastes have to be removed mechanically. Removal can either be carried out by grinding or by sandblasting. Here, the great disadvantage in the removal of the paste residues is the mechanical surface damage of the restoration part, which can thereby lead to a reduction of the mechanical strengths.

Furthermore, it is known from DE 103 39 246 A1 to employ a heat protection paste which breaks down in the thermal treatment of a dental product made of materials having stresses resulting from different heat expansion coefficients to the extent that no stress cracks or even spalling occur. This heat protection paste consists of water, diethylene glycol, temperature-resistant fibers and suitable heat-resistant fillers. The heat-related warpage of the molded parts is not taken into consideration in this reference.

DE 198 53 949 A1 describes a sinterable ceramic composition for sintering together individual crowns and bridge segments to form a single strong dental restoration.

US 2003/0059742 A1 describes the use in dental implants of mineral nanofibers 0.1-100 nm in size. In this use, these nanofibers are sintered to form shaped articles, or implants composed of other materials become coated with these nanofibers. These sintered nanofibers are notable for good osteointegration.

Similar basic components to those in the present invention are described in EP 0 464 545 A2. However, such a composition would not work as a supporting paste since the formulation after the burning out of the organic paste exhibits excessive contraction in volume and there is no supporting effect.

DE 36 10 844 C2 discloses a further development of dental cements which set to form a strong cementaceous material having compressive strengths of >600 bar. It is desirable for cements that they possess good bonding to the components to be cemented.

DE 14 67 061 A1 discloses using starting materials such as zinc and iron. These can lead at high temperatures to reactions with the glassy or glass-ceramic moldings which, in turn, trigger color impairments or even chemical reactions which lead to surface disruptions and thus to strength losses.

From DE 198 53 949 A1, it is known for the connection of dental restoration parts to employ connecting members which are sintered by a glass powder paste. This paste or suspension serves here for the mechanically solid connection between restoration part and connecting member.

From the company Functional Designs, Inc. (USA), a supporting paste with the name Easy Fix is on the market, which is composed as follows:

| | |
|---|---|
| water | 65-70% |
| aluminum silicate fibers | 20-25% |
| amorphous silicon dioxide | 5-10% |
| hydroxyethylcellulose | 1-3%. |

This paste fulfils the requirements with respect to the supporting function, but the fibers and the silicon dioxide adhere to the inside of the parts to be supported. The residues of the supporting paste remaining on the molded part must be removed using a particle blasting process (usually glass or glass ceramic powder). This process leads to damage to the surface structure and thus often to a decrease in strength of the entire molded part.

In the manufacture of dental restoration parts from only partly sintered zirconium dioxide, dense sintering is carried out at temperatures of about 1500° C. For this, it is likewise necessary to support this restoration part in the sintering process. For this purpose, various possibilities are known and in use.

Support can be carried out, for example, by intercalating the restoration part in a bed of thermally high-strength ceramic spheres or alternatively by "laying" the restoration part on pins which are arranged moveably and on shrinkage as a result of the sintering process compensates the shrinkage by inclining relative to one another. A further possibility, according to EP 0 817 597 B1, is to support the restoration part in a bed of the same partly sintered ceramic material which not only has a supportive effect, but at the same time has the same shrinkage as the restoration part.

A disadvantage in the previously known embodiments is that handling is complicated and that co-ordinated supporting systems have to be used for each application.

SUMMARY OF THE INVENTION

The object of the invention is to make available a paste which is inexpensive, thermally stable and does not adhere to the molded part, which exerts a reliable supporting function in the thermal treatment of glassy and/or glass ceramic molded parts and guarantees the geometrical stability of the molded part on sintering and/or crystallizing. Moreover, the supporting pastes should be able to be employed for the support of inorganic molded parts which have to be heated close to the softening or melting point in necessary sintering and/or crystallization processes in order to ensure their accuracy of fit.

The object according to the invention is met by a supporting paste containing a component (A), which loses water in a temperature range between 110° C. and 1100° C.,
a component (B), which is geometrically stable between 110° C. and 1100° C.,
a solvent,
auxiliary agents and additives.

The various features of novelty which characterize the invention are pointed out with particularity in the claims annexed to and forming a part of the disclosure. For a better understanding of the invention, its operating advantages, specific objects attained by its use, reference should be had to the descriptive matter in which there are illustrated and described preferred embodiments of the invention.

DETAILED DESCRIPTION OF THE PREFERRED EMBODIMENTS

Component (A) is preferably present according to the invention in powder form and as such is preferably water-insoluble.

The proportion of component (A) in the supporting paste is preferably 1-70% by weight, particularly preferably 20-70% by weight.

Component (A) preferably contains those inorganic substances which lose water on temperature increase. Hydroxides, hydrated oxides and/or compounds containing water of crystallization are particularly suitable for this purpose. Aluminum hydroxide, hydrated aluminum oxide and magnesium hydroxide and their mixtures are especially suitable.

The substances contained in component (A), in particular the inorganic substances contained therein, should preferably be thermally stable, but at least can change into a thermally stable form on temperature increase. Furthermore, it is advantageous if no ions are introduced which enter into a chemical reaction with the molded part or lead to discolorations.

Preferably, compounds are employed in component (A) in which the release of water takes place over a wide temperature range. Such properties are to be found, in particular, in inorganic oxides, hydroxides and/or from salts comprising water of crystallization. For example, the combustion loss of aluminum hydroxide according to ISO 806 takes place in a temperature range between 110° C. and 1100° C. and is in this case about 35% by weight. Here, the aluminum hydroxide changes after complete removal of water to thermally and chemically inert aluminum oxide. As a result of the release of the water from component (A) or from the inorganic substances contained therein, their volume also decreases. This simultaneously assists the compensation of the heat expansion of the supporting paste. As a result, stresses are also prevented which can be built up by the different heat expansion coefficients during the heating phase and result during the cooling of the system molded part/supporting paste after carrying out the sintering/crystallization and can also lead here to geometric deformations of the molded part.

The disclosure of the use by way of example of aluminum hydroxide is thus to be seen in that during processing a mass loss and thus also a volume reduction of component (A) occur. According to the invention, it is therefore advantageous to reduce this volume reduction by means of further components or to adjust it to a specific value.

According to the invention, the supporting paste contains a component (B) as a further filler. For this, fillers are preferably employed which show virtually no change in volume during the thermal processes and are employed depending on the predicted temperature range of the sintering/crystallization. In particular, glass, glass ceramic, $SiO_2$, $Al_2O_3$, $ZrO_2$ or MgO powder are used according to the invention. Care is to be taken here that none of the components (A) or (B) used enters into a chemical reaction with the molded part to be supported or leads to its discoloration.

The proportion of component (B) is preferably 8 to 80% by weight, particularly preferably 9 to 60% by weight.

The supporting paste according to the invention is prepared by adding 5% to 70% by weight, preferably 10% to 49% by weight, more preferably 10% to 40% by weight and most preferably 20% to 35% by weight of solvent. To this end according to the invention components (A) and optionally (B) are mixed with water and/or an organic solvent which burns without residue into a paste. Suitable organic solvents are, for example, alcohols, ketones or liquid aliphatics.

In order to improve the homogeneity and smoothness of the pastes, the paste according to the invention may preferably contain 0% to 15% by weight of auxiliary agent and more preferably 0.1% to 10% by weight of auxiliary agent.

Thus, it has been found that, by the use of highly disperse metal oxides, pastes are obtained which can be easily applied and have an excellent storage stability. Usually, these metal oxides are prepared from the corresponding halides or alcoholates by means of flame pyrolysis and have a very small primary particle size. Examples of such highly disperse metal oxides are, for example, aluminum oxide (Alox® C) or silicon dioxide (Aerosil®), both from Degussa AG.

The advantage of these inorganic thickeners is that, in contrast to the organic thickeners, they do not burn out and thus lead to no additional volume shrinkage.

Furthermore, there is no risk that any possible sooty residues remain after burning which would lead to soiling or even permanent discoloration of the molded part.

Further important criteria for the degree of filling and the consistency of the paste are the particle sizes of the fillers and their thickening action in the particular purely inorganic or inorganic/organic system. Particle sizes of 10 to 500 nm are best suited as thickeners and are applicable for a homogeneous storage-stable consistency. Particles having particle sizes over 0.5 m are very highly suitable in order to achieve high degrees of filling and thus high dry residues. Meanwhile, particle sizes of over 50 m lead to a sandy and thus poorly measurable consistency. In order to avoid premature drying out of the pastes, it can be advantageous to employ soluble organic substances or inorganic salts.

If aqueous systems of neutral pH are desired, it is useful to adjust the mixture of, for example, hydrated aluminum oxide and pyrogenic aluminum oxide to the desired pH.

Components (A), (B) and optionally the further auxiliary agents and additives and also binders can be mixed in the presence of the abovementioned solvents to give a paste by means of suitable machines e.g. kneading machines and paste machines.

Preference is finally also given to the addition of 0% to 20% by weight of binders. Preferred binders are low-melting waxes, polyethylene glycols or mixtures thereof.

The stated weight percentages of components (A), (B), solvent, auxiliary and binder total 100% by weight.

From the abovementioned components, combustible and supporting pastes can be prepared which function optimally up to a temperature of approximately 1100° C., enter into no reactions with the molded parts of glasses or glass ceramics and lead to no discolorations. Furthermore, the paste residues can be removed easily from the surface of the molded parts after the crystallization or sintering processes.

Below, various compositions are indicated for those pastes which characterize the invention. These examples do not, at the same time, limit the invention.

TABLE 1

Compositions for combustible and supporting pastes (details in % by weight)

| Component | 1 | 2 | 3 | 4 | 5 | 6 | Comparison paste |
|---|---|---|---|---|---|---|---|
| Water (deionized) | 23.10 | 25.90 | 27.00 | 27.80 | 24.50 | 29.00 | 65-70 |
| $Al_2O_3$ (Alox® C)[1] | — | 8.00 | 6.00 | 3.10 | — | 3.20 | — |
| $SiO_2$ (Aerosil® 200)[2] | — | — | — | — | 9.10 | — | — |
| Amorphous $SiO_2$*[) | — | — | — | — | — | — | 5-10 |
| Aluminum hydroxide[3] | 67.30 | 21.40 | — | 25.80 | — | — | — |
| Magnesium hydroxide[4] | — | — | 25.00 | — | — | — | — |
| Aluminum oxide powder[5] | — | — | — | 43.30 | — | — | — |
| Quartz powder[6] | 9.60 | 44.50 | 42.00 | — | 66.40 | 67.80 | — |
| Hydroxyethylcellulose[7] | — | 0.20 | — | — | — | — | 1-3 |
| Aluminum silicate fibers*[) | — | — | — | — | — | — | 20-25 |

Details for the raw materials used:
[1] Aerosil ALU C Degussa, average primary particle size 13 nm, BET surface area 100 ± 15 $m^2/g$
[2] Aerosil 200 Degussa, average primary particle size 12 nm, BET surface area 200 ± 25 $m^2/g$
[3] aluminum hydroxide purum; Fluka Art. No. 11033
[4] magnesium hydroxide, very pure; MERCK Art. No. 5870
[5] aluminum oxide powder; special blasting abrasive Ivoclar AG
[6] quartz powder; Mikro-Dorsilit 405 ®, Dorfner, particle size 16 m
[7] hydroxyethylcellulose medium viscosity; Fluka Art. No. 54290
*) no details of the manufacturer available Preparation of the Pastes The pastes were prepared in a Linden kneader (Linden type LPM 2 SP) at room temperature.

The water, optionally containing a dissolved salt or cellulose, is introduced in the kneader. Subsequently, the Alox® C is mixed in homogeneously for 30 minutes. In the next step, for example, the aluminum hydroxide is added and likewise mixed for 30 minutes. After this, for example, quartz powder is incorporated in portions and after the last addition the batch is mixed again for 30 minutes.

The desired theoretical consistency is subsequently measured by means of a penetrometer PNR 10 and the batch is optionally diluted with water or thickened with quartz powder. Gravity penetrometers are used for the determination of the consistency by means of the penetration depth. Here, a needle-like or conical pin is placed on the surface of the investigation material and then sinks into the test material during a defined time span under its own weight. The penetration depth is indicated in mm as a penetration unit and is a measure of the plasticity or consistency. The penetrometer PRN 10 used here is operated by the company Petrotest.

The homogeneity of the paste or complete disintegration of the agglomerates is checked by means of a grindometer (i.e. ZGR 2021 of Zentre)

Grindometers (method according to Hegman) are used for the determination of the grinding fineness (granularity or particle size) of coating substances, printing inks, pastes and similar products. In this case, the paste is filled into the deepest position of the grindometer channel and drawn in the direction of the flat end with a scraper. Subsequently it is determined from which channel depth the filler particles or agglomerates are additionally drawn by the scraper. This can clearly be seen by the track in the paste. Subsequently, the fineness in m can be read off on the engraved scale on the edge of the grindometer. Customary channels are wedge-like running from 50 to 0 m.

The pastes prepared in this manner were tested in a ceramic firing kiln Programat® P200 (Ivoclar Vivadent AG). For this, an about 2-3 mm thick layer of the paste was spread onto a substrate of silicon nitrite, on which a ceramic crown filled with the supporting paste was placed. Afterwards, the supporting action of the paste was tested according to a combustion process customary for dental technology in the test arrangement. The combustion program was adjusted here as follows:
heating rate of 60 K/min to 850° C.
holding time of 10 min at 850° C.
cooling rate of 30 K/min to 700° C.
The combustion program can be carried out with or without vacuum. After the removal of the respective test crowns from the combustion chamber, the results using the various pastes were assessed as follows:

TABLE 2

Results of the experiments

| Example | Consistency of the paste | Adhesion of the paste to the inside | Supporting action at 850° C. |
|---|---|---|---|
| 1 | Good, stable | No adhesion | Good |
| 2 | Good, stable | No adhesion | Good |
| 3 | Good, stable | No adhesion | Good |
| 4 | Good, stable | No adhesion | Good |
| 5 | Slight flowing | Sticks strongly to the inside | Still acceptable fit accuracy |
| 6 | Good, stable | Sticks to the inside | Poor fit accuracy |
| 7 (comparison paste) | Good, stable | Sticks to the inside, forms residues on the surface | Good |

A discoloration of the crown, either on the inside or the outside, occurred in none of the pastes tested above.

The adhesion of the paste was only tested subjectively by scraping out the paste residues after the sintering or crystallization process with a metal spatula (dental modelling instrument) and was subsequently evaporated using a steam jet apparatus. The remaining paste residues can also be removed easily from the inside of the crown in a soap/water mixture by means of an ultrasonic bath.

The invention claimed is:
1. A method for sintering or crystallization of glassy or glass ceramic molded parts in the field of dental technology, comprising the steps of applying to the molded parts a supporting paste including 1% to 70% by weight of a component (A), which loses water in a temperature range between 110° C. and 1100° C., 8% to 80% by weight of a component (B), which is geometrically stable at temperatures between 110° C. and 1100° C., 5% to 70% by weight of solvent, 0% to 20% by weight of binder, and 0% to 15% by weight of further auxiliary agents and additives, the individual weight percentages totaling 100% by weight, wherein the component (A) is selected from the group consisting of aluminum hydroxide, hydrated aluminum oxide and magnesium hydroxide and their mixtures; and sintering or crystallizing the molded parts.

2. The method according to claim 1, wherein the supporting paste comprises from 8% to 50% by weight of component (A).

3. The method according to claim 1, wherein the supporting paste comprises from 20% to 80% by weight of component (B).

4. The method according to claim 1, wherein the supporting paste comprises 20% to 70% by weight of component (A), 9% to 60% by weight of component (B), 15% to 49% by weight of solvent, 0% to 20% by weight of binder, 0.1% to 10% by weight of further auxiliaries and additives, the individual weight percentages summing to 100% by weight.

5. The method according to claim 1, wherein component (B) of the supporting paste contains glass powder, glass-ceramic powder, $SiO_2$ powder, $Al_2O_3$ powder, $ZrO_2$ powder or MgO powder as fillers.

6. The method according to claim 1, wherein the supporting paste comprises water or organic solvents burning without a residue or mixtures thereof as solvents.

7. The method according to claim 1, wherein the supporting paste comprises alcohols, ketones, liquid aliphatics or mixtures of these substances as organic solvents.

8. The method according to claim 1, wherein the supporting paste comprises low-melting waxes or polyethylene glycol or mixtures thereof as binders.

9. The method according to claim 1, wherein the supporting paste comprises thickeners or lubricant auxiliaries as auxiliaries or additives.

10. The method according to claim 1, wherein the supporting paste comprises aluminum oxide or silicon dioxide or mixtures thereof as thickeners.

* * * * *